United States Patent [19]

Kayser et al.

[11] 4,315,506
[45] Feb. 16, 1982

[54] POSITIVE PULSE DEVICE

[75] Inventors: John P. Kayser, Madison; Norman A. Rick, Mt. Horeb, both of Wis.

[73] Assignee: Airco, Inc., Montvale, N.J.

[21] Appl. No.: 196,985

[22] Filed: Oct. 14, 1980

Related U.S. Application Data

[63] Continuation of Ser. No. 10,095, Feb. 7, 1979, abandoned.

[51] Int. Cl.³ .............................................. A61M 1/00
[52] U.S. Cl. ...................................... 128/276; 251/63
[58] Field of Search .................... 137/DIG. 8; 251/63; 417/146, 148, 137; 128/276–278, 297; 15/353

[56] References Cited

U.S. PATENT DOCUMENTS

| | | | |
|---|---|---|---|
| 3,429,313 | 2/1969 | Romanelli | 128/276 |
| 3,955,574 | 5/1976 | Rubinstein | 128/278 |
| 4,041,944 | 8/1977 | Rhodes | 128/278 |

FOREIGN PATENT DOCUMENTS

| | | | |
|---|---|---|---|
| 66491 | 4/1969 | German Democratic Rep. | 128/276 |
| 796724 | 6/1958 | United Kingdom | 128/276 |
| 307793 | 7/1971 | U.S.S.R. | 128/276 |

OTHER PUBLICATIONS

Catalog Cut "Snyder Laboratories" New Philadelphia, Ohio, Sep. 1969.

Primary Examiner—Robert W. Michell
Assistant Examiner—J. L. Kruter
Attorney, Agent, or Firm—Roger M. Rathbun; Larry R. Cassett

[57] ABSTRACT

A device for use in vacuum suction systems for withdrawing fluids from a patient's body cavity, such as the stomach, wherein the device includes a chamber that is located in the flow stream of such fluids between the patient and the source of vacuum. At predetermined intervals, the device forces a quantity of the withdrawn fluid from the chamber, back into the suction tubing leading to the patient such that some of the fluid previously removed from the body cavity is forced backward toward such cavity under a positive pressure to dislodge any obstructions that may have occurred in the tubing or at the end of such tubing. In the preferred embodiment, the device is effectively self-contained and needs no source of positive pressure or electricity for its operation and is readily and fully operable from present commercial intermittent suction systems without revamping or otherwise modifying existing systems.

6 Claims, 2 Drawing Figures

4,315,506

POSITIVE PULSE DEVICE

This is a continuation of application Ser. No. 10,095, filed Feb. 7, 1979, now abandoned.

BACKGROUND OF THE INVENTION

This invention relates to a device used for the withdrawal of fluids from patient cavities. More specifically, the present invention comprises a device that can be used with present suction systems where vacuum is utilized for fluid drainage and the new device serves to force a quantity of the evacuated fluid backwards towards the patient cavity at predetermined time intervals to free clogged material from the drainage tubing or catheter.

In most hospitals today, central vacuum systems are provided by pipeline to accessible outlets in the various treatment rooms. The vacuum is thereupon utilized for the withdrawal of fluids from patient cavities, particularly from stomach cavities in post-operative treatment.

One of the problems associated with patient drainage is, however, the clogging of catheters or tubing by mucous or other heavy matter being drained. Such clogging prevents the flow of fluids from the patient and requires attention by hospital personnel to vigilantly insure that all tubing to the patient remains clear of such obstructions.

In Intermittent Suction Units (ISU's) a feature is provided that attempts to automatically alleviate the clogging problem. ISU's are regularly used in hospital treatment for drainage of patient cavities and, in effect, such devices stop the vacuum on a predetermined cycle and open the tubing leading to the patient to atmospheric pressure. In this way, the flow of fluid from the patient is temporarily stopped and some of the fluid is allowed to run backward by gravitational forces toward the patient. Examples of typical ISU's are shown and described in Eichelman U.S. Pat. No. 3,086,528, Sielaff U.S. Pat. No. 3,659,605 and others.

Intermittent suction does effectively clear various obstructions from suction devices and tubing, however, it does have limitations, in particular, the flow backward to the patient relies significantly upon the effect of gravity and, in those cases where the clogging material is heavy mucous, there may not be enough gravitational effect to cause the necessary movement backward toward the patient, thus the material remains in its undesirable position in the various tubing.

A further improvement to dislodge clogging material has been to force a fluid backwards toward the patient under a positive pressure, with particular emphasis on the introduction of a liquid, such as a saline solution, into the patient tubing. An example of such a positive backflow system is described in Blanck U.S. Pat. No. 3,042,042. In the Blanck system, however, a separate fluid is required that is forced by a piston back into the tubing leading to the patient. The overall system is relatively complex and requires electrical power as well as a plurality of motor-operated values. Also, the introduction of an outside fluid requires attention to sterility conditions.

A further system for producing alternate pulsations may be found in Duron U.S. Pat. No. 1,755,318 but no backflow is contemplated.

In U.S. Pat. No. 3,955,574 there is described a system for producing positive pressure back pulses used with a patient drainage system, however, again the unit comprises a complete system requiring a source of vacuum as well as pressure and thus, is an attempt to replace present suction systems rather than complement them.

SUMMARY OF THE INVENTION

The present invention overcomes the difficulties of the aforedescribed systems by providing a relatively inexpensive, simple device that may be used with present suction systems to add on the feature of providing a positive pulse of fluid backward toward a patient at predetermined time intervals to clear obstructions from tubing and/or catheters. The device is readily adapted to operate in connection with normal ISU's and basically changes the operation of that system from a gravity induced backward fluid movement to one that actually forces fluid backward under a positive controlled pressure.

In the preferred embodiment, the device of this invention requires no additional source of power for its operation, i.e. no pressure source is needed nor is any electrical power required.

Since the fluid forced backward is the same fluid previously withdrawn from the patient cavity, the problems of sterility in introducing an outside liquid are eliminated.

The device of the present invention is characterized by the inclusion of a chamber into the vacuum tubing line running from a patient to the source of intermittent vacuum. As the normal vacuum is interrupted by the ISU, the present device automatically senses the cessation of vacuum and closes off the tubing leading from the device to the ISU. The chamber is thereupon isolated from the vacuum source but is open to the patient cavity. Fluid in the chamber is then forced from that chamber and moves back through the open tubing toward the patient. In the preferred form, the chamber is essentially collapsed to force the fluid contained therein backwards toward the patient.

By this means, the device of the present invention can readily be installed in existing intermittent suction systems without the attendant high costs of installing an entirely new system to obtain a backward positive pulse of fluid, nor is any independent timing system needed. In fact, the cost of such a device can be made low enough to the point that the device itself is readily disposable and thus need not be autoclaved or otherwise cleaned after use.

BRIEF DESCRIPTION OF THE DRAWINGS

The improved positive pulse device is illustrated in the accompanying drawings which show the preferred embodiment of the invention, incorporating the features and advantages described.

DESCRIPTION OF THE PREFERRED EMBODIMENT

Figure 1:
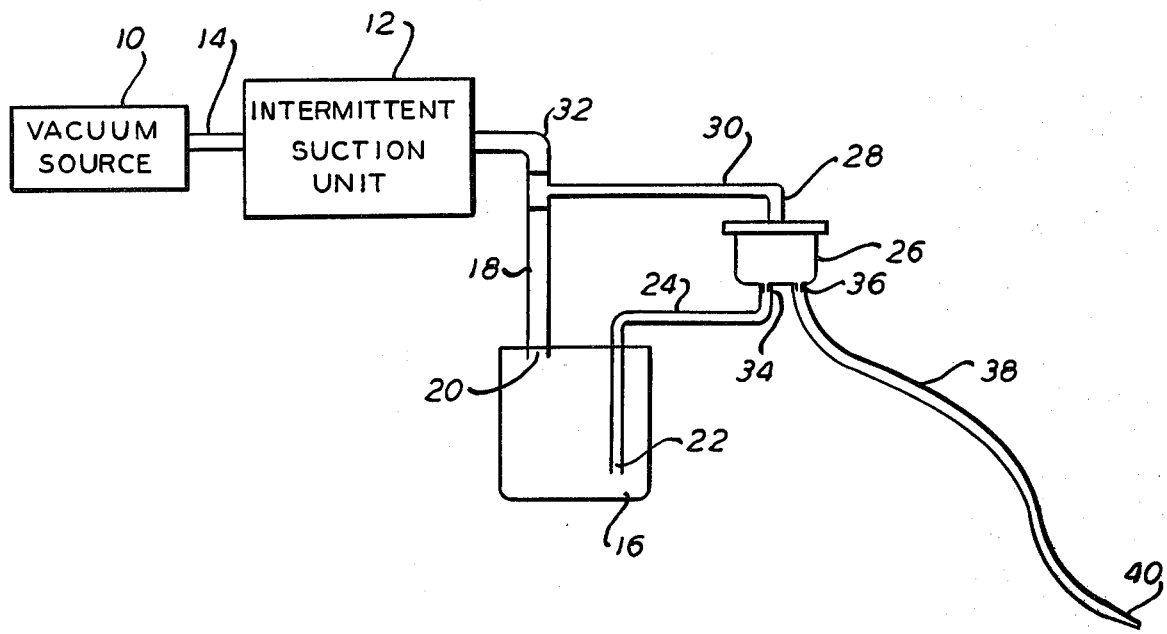
FIG. 1 is a flow diagram showing the device of the present invention installed in a conventional intermittent suction system.

Referring now to FIG. 1, there is shown a flow diagram with a device made in accordance with the present invention incorporated into a typical intermittent suction system for fluid removal from a patient.

A vacuum source 10 provides a regulated vacuum for operation of the suction system. Typically, hospitals are equipped with pipeline vacuum supply where a central vacuum pump is interconnected to individual rooms where outlets are installed that receive suitable plugs for use of the vacuum in various equipment. The normal vacuum found in most hospitals generally range to about 29 inches of Hg.

Connected to the vacuum source 10 is an intermittent suction unit or I.S.U. 12, typical of which is the fluidic unit described in U.S. Pat. No. 3,659,605 of U. Sielaff. As shown in the FIG. 1, a suitable tube 14 is used, however, in commercial units, the ISU 12 generally plugs directly into and is carried by the vacuum outlet in the treatment room.

A collection bottle 16 receives the drainage fluids from the patient and is connected to ISU 12 by suitable tubing 18. The collection bottle 16 normally collects fluids and in turn provides protection to prevent fluids from reaching a point downstream of the collection bottle 16 where such fluid could enter and do damage to the ISU 12 or vacuum source 10. As shown, the collection bottle 16 includes an outlet 20 where vacuum is drawn and an inlet 22 where fluids that are removed from the patient are deposited in the bottle 16.

Connected to the bottle inlet 22 by suitable tubing 24 is the positive pulse device 26 which is the subject of this invention. The device 26 has a vacuum port 28 which is connected by suitable tubing 30 to the output of the ISU 12. As shown, this is readily accomplished by a tee 32 in tubing 18 leading from the ISU 12. The positive pulse device 26 also has a bottle port 34 connected to the collection bottle 16 by tubing 24 and a patient port 36 again connected by tubing 38 to a device such as a catheter 40 which is inserted within the patient cavity when the drainage operation is being carried out.

Figure 2:
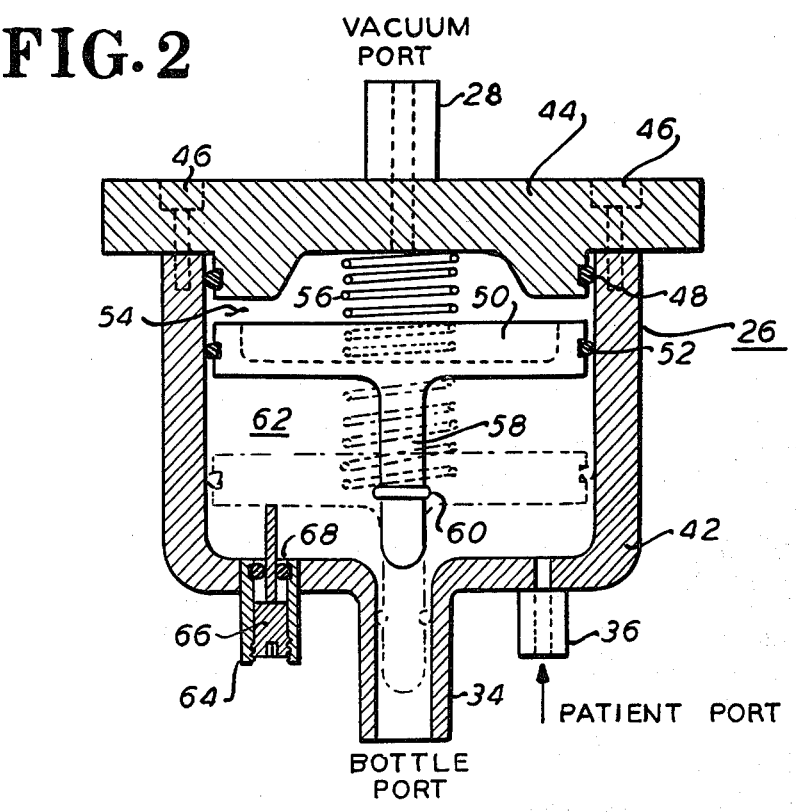
FIG. 2 is a cross-sectional view showing the actual configuration of the device constructed in accordance with the present invention.

The purpose and functions of the various ports of the pulse device 26 will become apparent from an explanation of FIG. 2 showing a cross-sectional view thereof showing a solid line position and a dotted line position of the pulse device 26.

The pulse device 26 depicted in FIG. 2 has the vacuum port 28, patient port 36 and bottle port 34 in their respective positions and comprises a frame 42 and a lid 44 which is fitted atop frame 42 forming an enclosed volume therein. The lid 44 may be tightly retained against the frame 42 by means such as screws 46 and an adequate seal is provided by means such as O-ring 48 to insure that the lid 44 is fully sealed about the top surface of the frame 42.

A movable piston 50 is positioned within frame 42 and is sealed by an O-ring 52 against the inner surface thereof. As may now be seen, a sealed vacuum chamber 54 is thus formed between the upper area of piston 50 and the lid 44. A spring 56 engages the piston 50 and lid 44 and exercises a bias to push the piston 50 away or downwardly from lid 44, the purpose of which will later be explained.

The piston 50 has an elongated nose 58 which extends downwardly toward bottle port 34. As shown in the solid line position in FIG. 2, the nose 58 is not in engagement with bottle port 34, however, in the dotted line position, the nose 58 is positioned within bottle port 34 and O-ring 60 seals the nose 53 against the inside surface of the bottle port, thereby closing the bottle port 34. As also may be seen, the underside of the piston 50 forms a fluid chamber 62 with the frame 42 wherein the only openings into said fluid chamber 62 are the patient port 36, and, depending upon the position of the piston 50, the bottle port 34 may or may not also consititute an opening into fluid chamber 62.

Also found in the lower portion of frame 42 is a cylindrical housing 64 having an internal threaded portion. A pin 66, also being suitably externally threaded, fits within housing 64 and moves laterally with respect thereto when said pin 66 is rotated in either direction. An O-ring 68 seals the pin 66 against the internal surface of frame 42 to prevent leakage from the fluid chamber 62.

At the lower end of pin 66, some means is provided for engagement with a turning tool; one possible configuration is an allen wrench socket so that an allen wrench may be fitted thereto and, when rotated, can advance or withdraw pin 66 with respect to the fluid chamber 62.

Turning now to the operation of the pulse device 26, it may be seen that in the solid line position of piston 50, fluid from the patient is drawn into the fluid chamber 62 through patient port 36 and is continually withdrawn therefrom through vacuum being applied via the bottle port 34. The fluid thus flows through the fluid chamber 62 in this position as the same is withdrawn from the patient to the collection bottle 16. At this point of the operation, it is assume that the ISU 12 is in the sucking position and vacuum is thus being applied continuously to the bottle port 34. The vacuum is, however, also being applied to the vacuum port 28 of the pulse device 26 and thus evacuates the vacuum chamber 54 to hold the piston 50 upwardly against the bias of spring 56.

As the ISU 12 enters the off cycle, i.e. the supply of vacuum is stopped, the ISU 12 causes the pressure in tubing 18 to return to atmospheric pressure and, accordingly, the vacuum chamber 54 also returns to atmospheric pressure.

The spring 56 thus applies its bias or force against the piston 50 serving to push the piston 50 downwardly. As piston 50 progresses downwardly, the piston nose 58 initially enters bottle port 34 and closes that port off by sealing O-ring 60 against the internal surface of bottle port 34.

As piston 50 continues its progress downwardly, the fluid remaining in the fluid chamber 62 is thus confined within a collapsing chamber and such fluid is forced out the patient port 36 backwardly toward the patient, thus effecting a positive pressure pulse of fluid in the reverse direction of normal fluid withdrawal to dislodge any obstructions in the tubing 38 or catheter 40.

As the ISU 12 again switches to the "on" or suction cycle, the vacuum chamber 54 is again evacuated and the piston 50 moves upwardly to return to the solid line position.

An adjustment to the stroke of piston 50 is accomplished by turning pin 66 which moves the pin with respect to piston 50 and limits the bottom of the piston stroke. As the pin 66 is rotatably inwardly, therefore, the piston stroke is decreased. In this manner, the attending personnel can set and adjust the quantity of fluid which is forced backwardly toward the patient.

Thus, as may be seen, the positive pulse device 26 is readily installed in existing intermittent suction systems without any difficult circuit changes and is completely powered by the vacuum source provided; no external source of energy, such as a pressure source, is necessary. Also, since the device 26 merely returns to the patient some of the fluid previously withdrawn, no additional sterile liquid is necessary.

It will be understood that the scope of the method and product of this invention is not limited to the particular steps or materials disclosed herein, by way of example, but only by the scope of the appended claims.

We claim:

1. A positive pulse device operable from a vacuum source and adapted to be located in a patient drainage line leading from a patient to the vacuum source, said device comprising an enclosed housing, a movable piston within said housing separating the interior of said housing into first and second chambers, said second chamber having an inlet for receiving fluids from the patient and an outlet in communication with the vacuum source, said first chamber adapted to be connectible to said source of vacuum, bias means on said piston exerting a force thereon in a direction toward said second chamber, said first chamber being dimensioned such that vacuum applied to said first chamber overcomes said bias means to hold said piston in a first position withdrawn toward said first chamber, said first chamber being adapted to selectively be placed at atmosphere pressure causing said bias means to force said piston to move to a second position collapsing said second chamber, whereby fluids from the patient collected in said second chamber are forced therefrom in a backward direction toward the patient.

2. A positive pulse device as defined in claim 1 wherein said piston is adapted to close said outlet of said second chamber.

3. A positive pulse device as defined in claim 2 wherein said second chamber outlet comprises an opening in said enclosed housing, and wherein said piston further comprises a nose adapted to align with and enter said opening when said piston initially moves toward said second position whereby said nose closes said opening.

4. A positive pulse device as defined in claim 2 where means are included to control the total movement of said piston between its first and second positions.

5. A positive pulse device for use in a vacuum line connecting a patient to a source of vacuum for removal of fluids from the patient, said device comprising a variable chamber through which at least a portion of said fluid passes from the patient toward the vacuum source, said variable chamber having an expanded condition and a contracted condition and having an inlet for receiving fluids from the patient and an outlet connected to the source of vacuum, said variable chamber having means to be connected to said source of vacuum to move said chamber to its expanded position, and bias means to move said chamber to its contracted position when said further connection to said source of vacuum is discontinued whereby a portion of said fluid contained within said chamber is forced from said chamber backwardly through said inlet toward said patient.

6. A method of returning a portion of fluid being withdrawn from a patient toward a vacuum source comprising the steps of:
   (a) positioning an expandable-contractible chamber within the flow path of fluids being withdrawn from the patient;
   (b) directing the flow of at least a portion of such fluids through said chamber;
   (c) selectively applying a vacuum to said chamber to expand said chamber; and
   (d) selectively terminating vacuum to said chamber to contract said chamber to force a portion of the fluid contained therein withdrawn from the patient in a direction backward toward the patient.

* * * * *